United States Patent
Ruiz Riol et al.

(10) Patent No.: US 9,709,577 B2
(45) Date of Patent: Jul. 18, 2017

(54) METHOD FOR MONITORING HIV SPECIFIC T CELL RESPONSES

(71) Applicants: LABORATORIOS DEL DR. ESTEVE S.A., Barcelona (ES); FUNDACIÓ PRIVADA INSTITUT DE RECERCA DE LA SIDA—CAIXA, Badalona (ES); INSTITUCIÓ CATALANA DE RECERCA I ESTUDIS AVAÇNATS, Barcelona (ES)

(72) Inventors: Marta Ruiz Riol, Badalona (ES); Christian Brander, Tiana (ES); Javier Ibarrondo, Culver City, CA (US)

(73) Assignees: LABORATORIOS DEL DR. ESTEVE S.A., Barcelona (ES); FUNDACIO PRIVADA INSTITUT DE RECERCA DE LA SIDA—CAIXA, Badalona (ES); INSTITUCIÓ CATALANA DE RECERCA I ESTUDIOS AVANÇATS, Barcelona (ES)

( * ) Notice: Subject to any disclaimer, the term of this patent is extended or adjusted under 35 U.S.C. 154(b) by 267 days.

(21) Appl. No.: 14/386,940

(22) PCT Filed: Mar. 22, 2013

(86) PCT No.: PCT/EP2013/056110
§ 371 (c)(1),
(2) Date: Sep. 22, 2014

(87) PCT Pub. No.: WO2013/139972
PCT Pub. Date: Sep. 26, 2013

(65) Prior Publication Data
US 2015/0057175 A1   Feb. 26, 2015

Related U.S. Application Data

(60) Provisional application No. 61/615,038, filed on Mar. 23, 2012.

(30) Foreign Application Priority Data

Mar. 23, 2012 (EP) .................................. 12382109

(51) Int. Cl.
G01N 33/68 (2006.01)
G01N 33/50 (2006.01)
G01N 33/569 (2006.01)

(52) U.S. Cl.
CPC ....... *G01N 33/6866* (2013.01); *G01N 33/505* (2013.01); *G01N 33/5091* (2013.01); *G01N 33/56988* (2013.01); *G01N 2333/15* (2013.01); *G01N 2333/52* (2013.01); *G01N 2333/525* (2013.01); *G01N 2333/54* (2013.01); *G01N 2333/555* (2013.01); *G01N 2800/52* (2013.01); *G01N 2800/56* (2013.01); *G01N 2800/60* (2013.01)

(58) Field of Classification Search
CPC ............. G01N 33/6866; G01N 33/505; G01N 2333/15
USPC ............................................................ 506/9
See application file for complete search history.

(56) References Cited

U.S. PATENT DOCUMENTS

| | | | | |
|---|---|---|---|---|
| 2005/0148023 A1* | 7/2005 | Thadhani | ............. | G01N 33/689 435/7.1 |
| 2010/0143454 A1* | 6/2010 | McLinden | ........... | C07K 14/005 424/450 |
| 2012/0276134 A1* | 11/2012 | Fraser | .................... | A61K 39/00 424/193.1 |

OTHER PUBLICATIONS

Adler, Michael, W., "ABC of AIDS, Range and natural history of infection", British Medical Journal, vol. 294, May 2, 1987, pp. 1145-1147.
Betts, Michael, R., et al., "HIV nonprogressors preferentially maintain highly functional HIV-specific CD8+ T cells", Blood, Jun. 15, 2006, vol. 107, No. 12, pp. 4781-4789.
Beyrer, Chris, et al., "Epidemiologic and biologic characterization of a cohort of human immunodeficiency virus type 1 highly exposed, persistently seronegative female sex workers in Northern Thailand", The Journal of Infectious Diseases, vol. 179, 1999, pp. 59-67.
Brander, Christian, et al., "Capturing viral diversity for in-vitro test reagents and HIV vaccine immunogen design", Current Opinion in HIV and AIDS, 2007, 2, pp. 183-188.
Brander, Christian, et al., "The challenges of host and viral diversity in HIV vaccine design", Current Opinion in Immunology 2006, 18: 430-437.
Chattopadhyay, Pratip, K., "Good cell, bad cell: flow cytometry reveals T-cell subsets important in HIV disease", Cytometry Part A, 2010, 77A(7), pp. 614-622.
Deeks, Steven, G., et al., "Human immunodeficiency virus controllers: mechanisms of durable virus control in the absence of antiretroviral therapy", Immunity 27, Sep. 2007, pp. 406-416.
Ferre, April, L., et al., "Muscosal immune responses to HIV-1 in elite controllers: A potential correlate of immune control", Blood, 2009, 113(17), pp. 3978-3989.
Frahm, Nicole, et al., "Increased sequence diversity coverage improves detection of HIV-specific T cell responses", Journal of Immunology, vol. 179, 2007, pp. 6638-6650.
Gaschen, Brian, et al., "Diversity considerations in HIV-1 vaccine selection", Science, 2002, vol. 296, pp. 2354-2360.
Hunt, Peter, W., et al., "A low T regulatory cell response may contribute to both viral control and generalized immune activation in HIV controllers", Plos One, Jan. 2011, vol. 6, Issue 1, e15924, pp. 1-10.

(Continued)

*Primary Examiner* — Karla Dines
(74) *Attorney, Agent, or Firm* — Hueschen and Sage

(57) ABSTRACT

The invention relates to a method and a diagnostic kit for monitoring HIV specific T cell responses and identifying subjects capable of controlling HIV progression or preventing HIV infection altogether. The method is based on the combined use of boosted flow cytometry and toggle peptides and can cover a large set of effector functions. The method is also suitable to detect T cell responses of any desirable cytokine or combination of cytokines to any pathogen.

13 Claims, 11 Drawing Sheets

(56) References Cited

OTHER PUBLICATIONS

International Search Report for PCT/EP2013/056110 dated May 31, 2013.

Kolls, Jay, K., et al., "The role of Th17 cytokines in primary mucosal immunity", Cytokine & Growth Factor Reviews, 2010, 21, pp. 443-448.

Lamoreaux, Laurie, et al., "Intracellular cytokine optimization and standard operating procedure", Nature Protocols, vol. 1, No. 3, 2006, pp. 1507-1516.

Legrand, Fatema, A., et al., "Strong HIV-1-specific T cell responses in HIV-1-exposed uninfected infants and neonates revealed after regulatory T cell removal", Plos One, Dec. 2006, Issue 1, e102, pp. 1-10.

Lünemann, Jan, D., et al., "EBNA1-specific T cells from patients with multiple sclerosis cross react with myelin antigens and co-produce IFN-γ and IL-2", Journal of Experimental Medicine, Jul. 28, 2008, vol. 205, No. 8, pp. 1763-1773.

Meij, Pauline, et al., "Identification and prevalence of CD8+ T-cell responses directed against Epstein-Barr virus-encoded latent membrane protein 1 and latent membrane protein 2", Int. J. Cancer, 2002, 99, pp. 93-99.

Richmond, Meika, et al., "Epitope mapping of HIV-specific CD8+ T cell responses by multiple immunological readouts reveals distinct specificities defined by function", Journal of Virology, 85(3), 2011, pp. 1275-1286.

Roederer, Mario, et al., "SPICE: Exploration and analysis of post-cytometric complex multivariate datasets", Cytometry Part A, 79A, 2011, pp. 167-174.

Yusim, Karine, et al., "Clustering patterns of cytotoxic T-lymphocyte epitopes in human immunodeficiency virus type 1 (HIV-1) proteins reveal imprints of immune evasion on HIV-1 global variation", Journal of Virology, Sep. 2002, pp. 8757-8768.

Zhou, Wendi, et al., "Impact of donor CMV status on viral infection and reconstitution of multifunction CMV-specific T cells in CMV-positive transplant receipients", Blood, 2009, 113, pp. 6465-6476.

* cited by examiner

|  | CD8 T cells | | | | CD4 T cells | | | |
|---|---|---|---|---|---|---|---|---|
|  | Controls | Non-controllers | EC/VC | T-cell p-value | Controls | Non-controllers | EC/VC | T-cell p-value |
| Total CD8 Responses | 84 | 63 | 43 |  | 30 | 49 | 57 |  |
| CD107+ | 29 | 12 | 6 |  | 8 | 8 | 4 |  |
| CD69/TNF | 11 | 11 | 4 | $\chi^2$=33.16 | 3 | 13 | 16 | $\chi^2$=12.59 |
| Th1+ | 1 | 1 | 11 | p<0.001 | 3 | 0 | 5 | p=0.013 |
| Total Th1 boosted staining panel | 41 | 24 | 21 |  | 14 | 21 | 25 |  |
| CD107+ | 21 | 11 | 5 |  | 8 | 10 | 4 |  |
| CD69/TNF | 15 | 13 | 3 | $\chi^2$=15.90 | 1 | 4 | 11 | $\chi^2$=11.04 |
| Th2/17+ | 7 | 15 | 14 | p=0.003 | 7 | 14 | 17 | p=0.026 |
| Total Th2/17 boosted staining panel | 43 | 39 | 22 |  | 16 | 28 | 32 |  |

FIG. 3B

METHOD FOR MONITORING HIV SPECIFIC T CELL RESPONSES

FIELD OF THE INVENTION

The invention relates to a method and a diagnostic kit for monitoring HIV specific T cell responses and identifying subjects capable of controlling HIV progression or preventing HIV infection altogether.

BACKGROUND OF THE INVENTION

Human immunodeficiency virus (HIV) sequence diversity is a major hurdle for the reliable assessment of anti-viral T cell immunity in vitro and for the design of an effective and broadly applicable HIV vaccine. See Brander C, et al., Curr. Opin. Immunol. 2006; 18(4):430-437.

Despite the extensive HIV sequence diversity on a full genome level, the variation in individual positions of viral proteins is often restricted to a limited number of amino acid substitutions that recur or "toggle" throughout the different HIV clades. See Gaschen B, et al., Science 2002; 296:2354-2360. Toggling residues often include amino acid pairs such as arginine (R) and lysine (K) or leucine (L) and valine (V), which are biochemically similar and are, therefore, likely to be tolerated by the virus without serious impacts on its replication efficiency. Remarkably, most of Gag p24—representative of a highly conserved protein-toggled peptide mixtures only require fewer than 20 variants (median 4), even at the highest level of sequence coverage (i.e. only amino acids present in <5% of database sequence are excluded from toggle positions), while the number of variants is higher in other Gag subunits at this coverage. See Yusim K, et al., J. Virol. 2002; 76(17): 8757-8768. In an IFN-γ Elispot assay, it had been shown that these "toggle" peptides detect HIV specific CD4+ and CD8+ T cell responses of significantly higher breath and magnitude than matched consensus peptides. See Frahm N, et al., J. Immunol. 2007; 179:6638-6650.

Most of the studies of immunogen candidates for HIV vaccination are based in the analysis of IFN-γ production by Elispot. Until now, no direct correlation between magnitude or secretion of IFN-γ and viral load has been found. During the last years, it has been shown that the quality of the T cell responses against HIV antigenic determinants may be the key determinant in eliciting an effective response against the virus. However, the analysis of poly-functional responses (e.g. different cytokine secretion and perforate exocytose) of CD8+ T lymphocytes in HIV infected patients have shown a negative correlation between the polifunctionality capability of the T lymphocytes and viral load. In addition, flow cytometry and Elispot-based analyses may not detect responses associated to cytokines that are not measured regularly or that do not show expected effector function profile(s). Consequently, there is a need in the art for more sensitive and comprehensive methods for evaluating T cell response against HIV.

SUMMARY OF THE INVENTION

In a first aspect, the invention relates to a method for assaying the T cell response specific against a pathogen in a subject which comprises: i) contacting a sample comprising T cells from the subject with a composition comprising an antigen from the pathogen and ii) determining the levels of a plurality of cytokines produced by the T cells in the sample.

In a second aspect, the invention is related to a method for the identification of a highly exposed persistent seronegative patient comprising: i) incubating a sample containing T cells of said patient with a HIV or EBV peptide composition and ii) determining the levels of one or more cytokines selected from the group consisting of IL-1b, IL-5, IL-6, IL-9, IL-10, IL-12p70, IL-13, IL-17 and IL-22, wherein increased expression level of one or more of said cytokines with respect to a reference value is indicative that the patient is a highly exposed persistent seronegative patient.

In a third aspect, the invention relates to a kit comprising reagents for the detection of one or more cytokines selected from the group consisting of IL-1b, IL-5, IL-6, IL-9, IL-10, IL-12p70, IL-13, IL-17 and IL-22.

In a fourth aspect, the invention relates to method for the identification of a highly exposed persistent seronegative patient comprising: i) incubating a sample of said patient comprising T cells with a peptide composition derived from a HIV protein or from a EBV protein and ii) determining the Th1-like response, the Th2-like response or the Th17 response, wherein an increased Th1-like, Th2-like or Th17 response in said cells with respect to a reference value is indicative that the patient is a highly exposed persistent seronegative patient

DETAILED DESCRIPTION OF THE INVENTION

Figure 1:
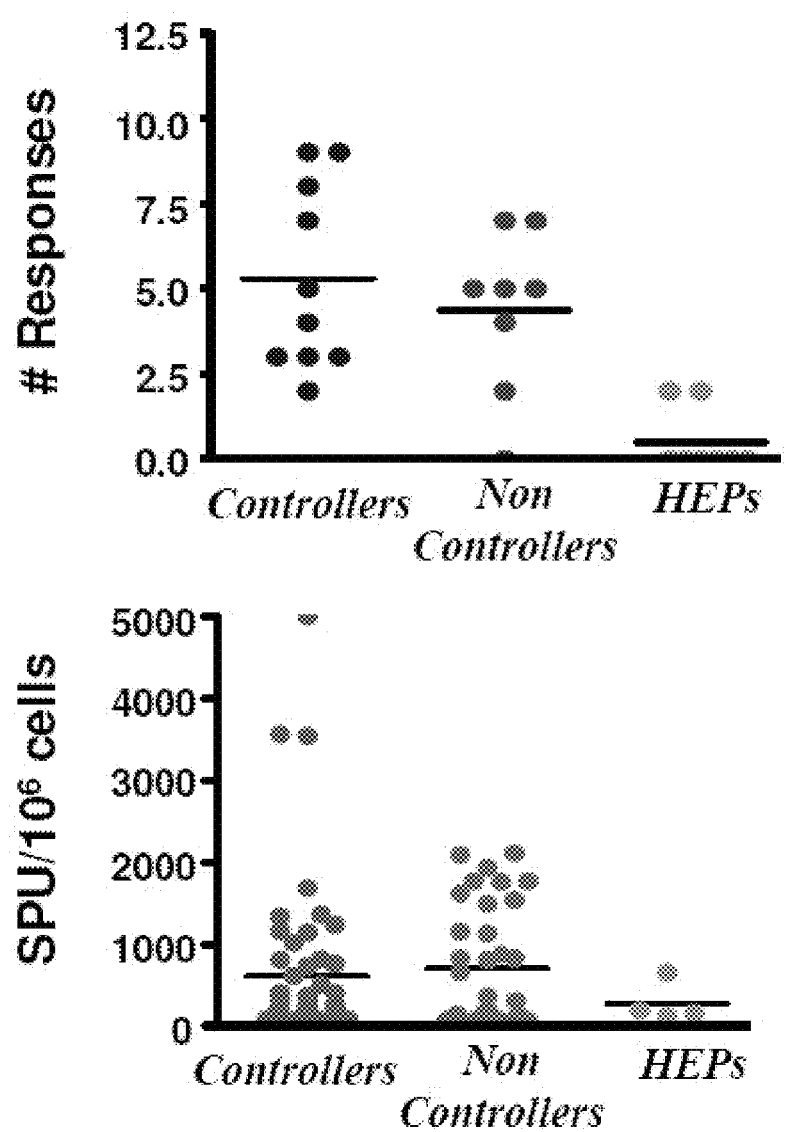
FIG. 1. Cellular responses due to Toggle peptide stimulation only. HIV patients showed higher responses, in terms of breath and magnitude than in HEPS individuals. No significant statistical differences between the controller and non-controller groups were observed. Fewer and weaker responses in the in HEPS group were also detected.

The present invention discloses a new method for assaying a cellular response against HIV. The method is based on the combined use of "boosted" flow cytometry ("Blow") and toggle peptides. The "Blow" analysis combines several cytokines into the same fluorescence channel and thus can cover a vastly larger set of effector functions than standard assays.

The combination of toggle peptides with the novel blow analysis and broad spectrum of cytokines in supernatants provides a powerful tool for a more comprehensive assessment of HIV specific T cell immunity, in general, and makes possible defining functional differences between HIV patients that controllers or non-controllers of the infection. The invention could be particularly helpful in detecting potentially "non-classical" effector functions and responses in vaccinated individuals, such as with dendritic cell vaccines, and in highly-exposed, persistently seronegative subjects (HEPS).

Surprisingly, the stimulation of a patient PBMCs with a Gag p24 or Gag p17 or Nef peptide, or with an EBV antigen, preferably a toggled peptide, in combination with the determination of cytokine levels by boosted flow cytometry, is a much more sensitive method for detecting specific lymphocyte T responses than the other methods described in the art such as the classic ELIspot of IFN-γ. This second method of the invention is specifically sensitive in detecting a Th1-like response in the HEPS population.

The inventors have observed that, surprisingly, the stimulation of PBMC of a patient with a Gag p24 or Gag p17 or Nef peptide variant population, or with an EBV antigen variant population, preferably a toggled peptide, and the determination of cytokine levels by boosted flow cytometry, is a much more sensitive method to detect specific lymphocyte T responses than classic ELISPOT of IFNγ. This second method of the invention is specifically sensitive in detecting a Th1-like response in the HEPS population.

The inventors have also observed that, surprisingly, the stimulation of PBMC of a patient with a Gag p24 or a Gag p17 or a Nef peptide variant population, or with an EBV antigen variant population, preferably a toggled peptide, and the determination of the levels of a plurality of cytokines by boosted flow cytometry, is a much more sensitive method to detect specific lymphocyte T responses than classic ELISPOT of IFN-γ.

The results of the present invention led to the conclusion that the technique of stimulation of PBMC with a peptide, followed by multiple-cytokine-detection using the boost flow cytometry method can be applied to any pathogen antigen capable of eliciting the production of cytokines in PBMC.

Finally, the present invention allows for the determination of specific peptide responses in CD4 (MHC class II peptides) as well as in CD8 (MHC class I peptides) and capture responses against HIV in HESN not observed so far.

Thus, in a first aspect, the invention relates to a method for assaying the T cell response specific against a pathogen in a subject which comprises: i) contacting a sample comprising T cells from the subject with a composition comprising an antigen from the pathogen and ii) determining the levels of a plurality of cytokines produced by the T cells in the sample.

In a preferred embodiment, the composition comprising an antigen is an antigen, more preferably a single antigen. In another embodiment, the composition comprising an antigen is a library of antigens.

In a preferred embodiment, the antigen from the pathogen is a peptide variant derived from a polypeptide of the pathogen. In another preferred embodiment, the library of antigens is a library of peptide variants. In a more preferred embodiment, the library of peptide variant is a toggled peptide.

In another preferred embodiment of the invention, the pathogen is HIV or EBV.

In case that the method of the invention is a method for assaying the T cell response specific against an HIV pathogen, the peptide variants derive from the Gag polyprotein or from the Nef protein. In a preferred embodiment, said peptide variants derive from p24 or p17.

In a preferred embodiment, the invention refers to a method for assaying the T cell response specific against a pathogen in a subject which comprises: i) contacting a sample comprising T cells from the subject with a library of peptide variants derived from a polypeptide of the pathogen and ii) determining the levels of a plurality of cytokines produced by the T cells in the sample.

In a preferred embodiment of the method of the invention the plurality of cytokines are selected from the group consisting of cytokines characteristic of a Th1 response, cytokines characteristic of a Th2 response and both. In a more preferred embodiment, the cytokines characteristic of a Th1 response are selected from the group consisting of IFN-γ, TNF-α, MIP1-β, IL-2, IL-12 and IL-1B. In another preferred embodiment, the cytokines characteristic of a Th2 response are selected from the group consisting of IL-4, IL-5, IL-6, IL-10, and IL-13. In another embodiment, the method of the invention further comprises determining the levels of cytokines characteristic of a Th9, Th17 or Th22 response.

In another preferred embodiment of the method of the invention the cytokines characteristic of a Th1 response, the cytokines characteristic of a Th2 response or both are determined in CD4+ cells and/or in CD8+ cells.

In a preferred embodiment of the method of the invention, the levels of a plurality of cytokines are determined by boosted flow cytometry. Several positive controls can be used in boosted flow cytometry. In a preferred embodiment, PMA (phorbol 12-myristate 13-acetate)+Io (ionomycine) is used as a positive control using the technique of boosted flow cytometry in HESN after a polyclonal stimulation. In another embodiment, EBV is used as a positive control using the technique of boosted flow cytometry in HESN after a monoclonal stimulation. The stimulation by EBV is peptide specific and it is therefore more similar to a stimulation with HIV peptides. Additionally, anti-CD3 plus anti-CD28 or PMA (or phorbol 12-myristate 13 acetate) plus Ionomicine (Io) may be used as positive controls. As additional positive controls for viral peptide stimulation, EBV MHC class I restricted peptide pool and EBV MHC class II restricted peptide pool for CD8 T cell and CD4 T cell stimulations, respectively, may also be used.

In a preferred embodiment, the sample containing T cell is a PBMC preparation.

In another aspect, the invention relates to a method for the identification of a highly exposed persistent seronegative patient comprising: i) incubating a sample containing T cells of said patient with a HIV or EBV peptide composition and ii) determining the levels of one or more cytokines selected from the group consisting of IL-1b, IL-5, IL-6, IL-9, IL-10, IL-12p70, IL-13, IL-17 and IL-22, wherein increased expression level of one or more of said cytokines with respect to a reference value is indicative that the patient is a highly exposed persistent seronegative patient.

In a preferred embodiment, the HIV peptide composition comprises peptides derived from Gag p24 HIV or Gag p17 HIV proteins. In a more preferred embodiment, the peptides derived from the Gag p24 HIV or Gag p17 HIV proteins are toggled peptides.

In a preferred embodiment, the sample containing T cells is a PBMC preparation.

In another preferred embodiment, the reference value for each cytokine is the expression level of said cytokines in a sample containing T cells from a HIV infected patient.

In another preferred embodiment, the determination of the cytokine levels is made by flow cytometry analysis. In a more preferred embodiment, the flow cytometry analysis is a boosted flow cytometry.

In another aspect, the invention relates to a kit comprising reagents for the detection of one or more cytokines selected from the group consisting of IL-1b, IL-5, IL-6, IL-9, IL-10, IL-12p70, IL-13, IL-17 and IL-22. In another aspect, the invention relates to the use of a kit of the invention for the identification of a HEPS patient according to the characteristics of the method of the invention.

In another aspect, the invention relates to a method for the identification of a highly exposed persistent seronegative patient comprising: i) incubating a sample of said patient comprising T cells with a peptide composition derived from a HIV or from a EBV protein and ii) determining the Th1-like response, the Th2-like response or the Th17 response, wherein an increased Th1-like, Th2-like or Th17 response in said cells with respect to a reference value is indicative that the patient is a highly exposed persistent seronegative patient.

In a preferred embodiment the Th1-like response is determined by measuring the levels of one or more cytokines selected from the group consisting of IFN-γ, TNF-α, MIP1-β, and IL-2; the Th2-like response is determined by measuring the levels of one or more cytokines selected from the group consisting of IL-4 and IL-10; or the Th17 response is determined by measuring the levels of Th17 (IL-17). In a more preferred embodiment, the determination of the cytokine levels is determined by boosted flow cytometry in CD4 and CD8 T lymphocytes.

In a preferred embodiment of a method of the invention for the identification of a highly exposed persistent seronegative patient, the HIV protein is p24 or p17. In another preferred embodiment, the HIV protein is p17. In a more preferred embodiment, the peptide composition is a toggled peptide mixture Thus, in another preferred embodiment, the invention relates to a method for the identification of a HEPS patient comprising incubating a sample of said patient with a peptide derived from Gag p24 HIV protein or Gag p17 HIV protein and determining the levels of Th1-like (IFN-γ, TNF-α, MIP1-β, IL-2), Th2-like (IL-4,-10) and Th17 (IL-17) cytokines by boosted flow cytometry in CD4 and CD8 T lymphocytes, wherein an increased expression level of any of said cytokines in CD4 T lymphocytes with respect to a reference value is indicative that the patient is a HEPS.

In a preferred embodiment of a method for the identification of a highly exposed persistent seronegative patient of the invention, the sample containing T cells is a PBMC preparation.

In a preferred embodiment of a method for the identification of a highly exposed persistent seronegative patient of the invention, the reference value is the level of Th1-like response, the Th2-like response or the Th17 response in a sample containing T cells from an infected patient.

1. Definitions

The term "AIDS", as used herein, refers to the symptomatic phase of HIV infection, and includes both Acquired Immune Deficiency Syndrome (commonly known as AIDS) and "ARC," or "AIDS-Related Complex". See Adler M, et al., Brit. Med. J. 1987; 294: 1145-1147. The immunological and clinical manifestations of AIDS are well known in the art and include, for example, opportunistic infections and cancers resulting from immune deficiency.

The term "antigen", as used herein, refers to a molecule capable of provoking an immune response. Antigens include but are not limited to cells, cell extracts, proteins, polypeptides, peptides, polysaccharides, polysaccharide conjugates, peptide and non-peptide mimics of polysaccharides and other molecules, small molecules, lipids, glycolipids, carbohydrates, viruses and viral extracts and muticellular organisms such as parasites and allergens. The term antigen broadly includes any type of molecule which is recognized by a host immune system as being foreign.

The term "antiretroviral therapy" or "ART", as used herein, refers to the administration of one or more antiretroviral drugs to inhibit the replication of HIV. Typically, ART involves the administration of at least one antiretroviral agent (or, commonly, a cocktail of antiretrovirals) such as nucleoside reverse transcriptase inhibitor (e.g. zidovudine (AZT, lamivudine (3TC) and abacavir), non-nucleoside reverse transcriptase inhibitor (e.g. nevirapine and efavirenz), and protease inhibitor (e.g. indinavir, ritonavir and lopinavir). The term Highly Active Antiretroviral Therapy ("HAART") refers to treatment regimens designed to aggressively suppress viral replication and progress of HIV disease, usually consisting of three or more different drugs, such as for example, two nucleoside reverse transcriptase inhibitors and a protease inhibitor.

The term "boosted flow cytometry" or "blow", as used herein, refers to an assay based on the detection of several cytokines in the same channel of fluorescence by flow cytometry, thus covering a vastly larger set of effector functions than standard assays.

The term "CD4(+) T cells" as used herein refers to T cells presenting a co receptor CD4 on their surface. The term refers to T helper cells, which either orchestrate the activation of macrophages and CD8+ T cells (Th-I cells), the production of antibodies by B cells (Th-2 cells) or which have been thought to play an essential role in autoimmune diseases (Th-17 cells). In addition, the term "CD4+ T cells" also refers to regulatory T cells, which represent approximately 10 percent of the total population of CD4+ T cells. Regulatory T cells play an essential role in the dampening of immune responses, in the prevention of autoimmune diseases and in oral tolerance.

The term "CD8(+) T cells" indicates T cells expressing the CD8 glycoprotein at their surface, wherein the CD8 (cluster of differentiation 8) glycoprotein is a transmembrane glycoprotein that serves as a co-receptor for the T cell receptor (TCR). Similarly to the TCR, CD8 binds to a major histocompatibility complex (MHC) molecule, but is specific for the class I MHC protein. Exemplary CD8 T cells comprise cytotoxic memory CD8 T cells, regulatory CD8 T cells, cytotoxic effector CD8 T-cells and additional cells identifiable by a skilled person.

The term "chronic progressor" or "non-controller", as used herein, refers to an individual that is infected with HIV and that exhibits and increase in viral load over time, following the initial infection.

The term "correlates" or "correlating" as used herein refers to a statistical association between instances of two events, where events may include numbers, data sets, and the like. For example, when the events involve numbers, a positive correlation (also referred to herein as a "direct correlation") means that as one increases, the other increases as well. A negative correlation (also referred to herein as an "inverse correlation") means that as one increases, the other decreases.

The term "cytokine" refers to small soluble proteins secreted by cells that can alter the behavior or properties of the secreting cell or another cell. Cytokines bind to cytokine receptors and trigger a behavior or property within the cell, for example, cell proliferation, death or differentiation. Exemplary cytokines include, but are not limited to, interleukins (e.g., IL-2, IL-3, IL-4, IL-5, IL-6, IL-7, IL-8, IL-9, IL-10, IL-11, IL-12, IL-13, IL-15, IL-16, IL-17, IL-18, IL-1a, IL-1 beta, and IL-1 RA), granulocyte colony stimulating factor (G-CSF), granulocyte-macrophage colony stimulating factor (GM-CSF), oncostatin M, erythropoietin, leukemia inhibitory factor (LIF), interferons, B7.1 (also known as CD80), B7.2 (also known as B70, CD86), TNF family members (TNF-alpha, TNF-beta, LT-beta, CD40 ligand, Fas ligand, CD27 ligand, CD30 ligand, 4-1BBL, Trail), and MIF. The cytokine levels can be determined by several methods well-known in the art, such as ELISA, ELISPOT, Western Blot, and flow cytometry. In a preferred embodiment, the determination of levels of cytokines for the method of the first aspect is made by Flow Cytometry.

As used herein, a highly exposed persistent seronegative (HEPS) patient refers to subject which, despite having evidence of multiple and repeated exposures to HIV-I through unprotected sexual contacts, possess no serum IgG reactive to the viral antigens (Beyrer, C. et al., J. Infect. Dis., 1999, vol. 79, pp. 59-68).

The term "variant", as used herein refers to i) variants of the polypeptide in which one or more of the amino acid residues are substituted by a conserved or non-conserved amino acid residue, wherein such substituted amino acid residue may or may not be one encoded by the genetic code, or ii) variants comprising an insertion or a deletion of one or more amino acids.

The term "EBV", also called Human herpesvirus 4 (HHV-4), is used throughout the specification to describe a herpetovirus found in cell cultures of Burkitts lymphoma. EBV is the causative agent in infectious mononucleosis, as well as in a number of other related conditions/disease states, including EBV-associated lymphomas The term "Gag p24 HIV protein", as used herein, refers to the capsid protein of the HIV, which is derived from the processed polyprotein Gag. In a preferred embodiment, the peptide derived from the Gag p24 HIV protein is a toggled peptide.

The term "Gag p17 HIV protein", as used herein, refers to the matrix that surrounds the capsid ensuring the integrity of the HIV virion particle. It is derived from the processed polyprotein Gag. In a preferred embodiment, the peptide derived from the Gag p17 HIV protein is a toggled peptide.

The term "Nef protein" refers to an accessory regulatory protein in HIV. In a preferred embodiment, the peptide derived from the Nef protein is a toggled peptide.

The term "highly-exposed, persistently seronegative" or "HEPS" or "HESN" individual, as used herein, refers to a subject exposed to HIV and who have not been infected with the virus. The presence or absence of HIV infection can be shown by demonstrating the presence of HIV antibody, HIV antigen, or HIV nucleic acid in the human subject as demonstrated by the detection of the presence of virus using HIV tests known to those skilled in the art (e.g. HIV EIA, Western blot, PCR tests).

The term "HIV", as used herein, include HIV-1 and HIV-2 and SIV. "HIV-1" means the human immunodeficiency virus type-1. HIV-1 includes but is not limited to extracellular virus particles and the forms of HIV-1 associated with HIV-1 infected cells. The HIV-1 virus may represent any of the known major subtypes (Classes A, B, C, D E, F, G and H) or outlying subtype (Group O) including laboratory strains and primary isolates. "HIV-2" means the human immunodeficiency virus type-2. HIV-2 includes but is not limited to extracellular virus particles and the forms of HIV-2 associated with HIV-2 infected cells. The term "SIV" refers to simian immunodeficiency virus which is an HIV-like virus that infects monkeys, chimpanzees, and other nonhuman primates. SIV includes but is not limited to extracellular virus particles and the forms of SIV associated with SIV infected cells.

The term "HIV exposure", as used herein, refers to the contact of a subject without an HIV infection or AIDS and a subject having an HIV infection or AIDS, or the contact with body fluids from such HIV-infected subject, in which such fluids from the infected subject contact a mucous membrane, a cut or abrasion in the tissue (e.g. needle stick, unprotected sexual intercourse), or other surface of the uninfected subject in such a way that the virus could be transmitted from the infected subject or infected subject's body fluids to the uninfected subject.

As used herein, "HIV infection" refers to indications of the presence of the HIV virus in an individual including asymptomatic seropositivity, AIDS-related complex (arc), and acquired immunodeficiency syndrome (AIDS).

The term "pathogen", as used herein, refers to a biological agent that causes a disease state (e.g., infection, cancer, etc.) in a host. "Pathogens" include, but are not limited to, viruses, bacteria, archaea, fungi, protozoans, mycoplasma, prions, and parasitic organisms.

The term "long term non-progressors", as used herein, refers to individuals who have been infected with HIV for approximately 10 years or longer, who are characterized by normal and stable levels of CD4+ T cells, and who have not been treated with antiretroviral therapy. These individuals comprise between the 5% and 15% of chronic HIV-infected persons. A more recent term related to long-term nonprogressors is "HIV controllers", which define non-progression based on plasma HIV RNA levels. There are two types of controllers "elite controllers" that exhibit undetectable plasma HIV RNA, and "viremic controllers" with detectable but low levels of plasma HIV RNA. See Deeks S, et al., Immunity 2007; 27:406-416 and Ferre A, et al., Blood 2009; 113(17):3978-3989.

The term "PBMC", as used herein, refers to peripheral blood mononuclear cells, including lymphocytes, monocytes and macrophages. Methods to isolate this PBMC from a blood sample are well known in the art.

The term "protease inhibitor", as used herein, refers to inhibitors of the HIV-1 protease, an enzyme required for the proteolytic cleavage of viral polyprotein precursors (e.g. viral GAG and GAG Pol polyproteins), into the individual functional proteins found in infectious HIV-1.

The term "reverse transcriptase inhibitors", as used herein, refers to any compound which inhibits the activity of HIV-1 reverse transcriptase, the enzyme which catalyzes the conversion of viral genomic HIV-1 RNA into proviral HIV-1 DNA.

The term "sample comprising T cells", as used herein, refers to tissues or bodily fluids removed from a mammal, preferably a human, and which contain T cells.

In some embodiments, the T cells are isolated from a mammalian sample prior to exposure to the peptide variants. The term "isolated" with respect to T cells refers to cell population preparation in a form that has at least 70, 80, 90, 95, 99, or 100 percent T cells. In some aspects, a desired cell population is isolated from other cellular components, in some instances to specifically exclude other cell types that may "contaminate" or interfere with the study of the cells in isolation. It is to be understood, however, that such an "isolated" cell population may incorporate additional cell types that are necessary for cell survival or to achieve the desired results provided by the disclosure. For example, antigen presenting cells, such as monocytes (macrophages) or dendritic cells, may be present in an "isolated" cell population of T cells or added to a population of isolated T cells for generation of regulatory T cells. In some aspects, these antigen presenting cells may be activated monocytes or dendritic cells. Cell populations comprising T cells for use in the methods of the disclosure may be isolated from a biological sample taken from a mammalian subject. The sample may originate from a number of sources, including, but not limited to peripheral blood, leukapheresis blood product, apheresis blood product, bone marrow, thymus, tissue biopsy, tumor, lymph node tissue, gut associated lymphoid tissue, mucosa associated lymphoid tissue, liver, sites of immunologic lesions (e.g., synovial fluid), pancreas, and cerebrospinal fluid. The donor subject is preferably human, and can be fetal, neonatal, child, adult, and may be normal, diseased, or susceptible to a disease of interest.

In some embodiments, the T cell sample comprises peripheral blood mononuclear cells (PBMCs) from a blood sample. By "peripheral blood mononuclear cells" or "PBMCs" is meant lymphocytes (including T-cells, B-cells, NK cells, etc.) and monocytes. In general, PBMCs are isolated from a patient using standard techniques. In some embodiments, only PBMCs are taken, either leaving or returning substantially all of the red blood cells and polymorphonuclear leukocytes to the donor. PBMCs may be isolated using methods known in the art, such as leukophoresis. In general, a 5 to 7 liter leukophoresis step is performed, which essentially removes PBMCs from a patient, returning the remaining blood components. Collection of the sample is preferably performed in the presence of an anticoagulant (e.g., heparin).

The T cell-containing sample comprising PBMCs or isolated T cells can be pretreated using various methods before the contacting with the peptide variant composition. Generally, once collected, the cells can be additionally concentrated, if this was not done simultaneously with collection or to further purify and/or concentrate the cells. For example, PBMCs can be partially purified by density gradient centrifugation (e.g., through a Ficoll-Hypaque gradient). Cells isolated from a donor sample are normally washed to remove serum proteins and soluble blood components, such as autoantibodies, inhibitors, etc., using techniques well known in the art. Generally, this involves addition of physiological media or buffer, followed by centrifugation. This may be repeated as necessary. The cells can then be counted, and in general, from $1 \times 10^9$ to $2 \times 10^9$ white blood cells are collected from a 5-7 liter leukapheresis. The purified cells can be resuspended in suitable media or buffer to maintain viability. Suitable solutions for resuspension will generally be a balanced salt solution (e.g., normal saline, PBS, Hank's balanced salt solution, etc.) optionally supplemented with fetal calf serum, BSA, HSA, normal goat serum, and/or other naturally occurring factors, in conjunction with an acceptable buffer at low concentration, generally from 5-50 mM. Convenient buffers include, but are not limited to HEPES, phosphate buffers, lactate buffers, etc.

The term "subject", as used herein, refers to an individual, plant or animal, such as a human, a nonhuman primate (e.g. chimpanzees and other apes and monkey species); farm animals, such as birds, fish, cattle, sheep, pigs, goats and horses; domestic mammals, such as dogs and cats; laboratory animals including rodents, such as mice, rats and guinea pigs. The term does not denote a particular age or sex. The term "subject" encompasses an embryo and a fetus. In a preferred embodiment, the subject is a human.

The term "Th1-like response", as used herein, relates to a response characterized by the production of IFN-γ, which activates the bactericidal activities of macrophages, and induces B-cells to make opsonizing (coating) antibodies, and leads to cell-mediated immunity. This response is also characterized by the production of TNF-α, MIP1-β and IL-2. Th1 responses are more effective against intracellular pathogens (viruses and bacteria that are inside host cells).

The term "Th2-like response", as used herein, relates to a response characterized by the release of IL-4, which results in the activation of B-cells to make neutralizing (killing) antibodies, leading to humoral immunity, and IL-10. Th2 responses are more effective against extracellular bacteria, parasites and toxins.

The term "T cell response" means an immune response in which T cells directly or indirectly mediate or otherwise contribute to an immune response in a mammal. The T cell mediated immune response may be associated with cell mediated effects, lymphokine mediated effects, etc., and even effects associated with B cells if the B cells are stimulated, for example, by the lymphokines secreted by T cells. For MHC class I restricted CTLs, effector functions may be lysis of peptide-pulsed, peptide-precursor pulsed or naturally peptide-presenting target cells, secretion of cytokines, preferably Interferon-gamma, TNF-alpha, or IL-2 induced by peptide, secretion of effector molecules, preferably granzymes or performs induced by peptide, or degranulation. For MHC class II-restricted T helper cells, effector functions may be peptide induced secretion of cytokines, preferably, IFN-gamma or IFN□, TNF-alpha or TNF□, IL-4, IL5, IL-10, or IL-2, or peptide-induced degranulation. Possible effector functions for CTLs and T helper cells are not limited to this list.

The term "toggled peptide", as used herein, refers to a peptide with significantly increased coverage of HIV sequence diversity by including alternative amino acids at variable positions during the peptide synthesis step. See Frahm N, et al., J. Immunol. 2007; 179: 6638-6650.

The term "Serodiscordant" refers to when two individuals in a couple present a discordant HIV serology, i.e. when one individual in the couple is infected (has the antibodies against in his blood) whereas the other is not.

The term "EBV" refers to Epstein-Barr virus, which is the virus causing infectious mononucleosis.

The term "kit", as used herein, refers to a product containing the different reagents necessary for carrying out the methods of the invention packed so as to allow their transport and storage. Materials suitable for packing the components of the kit include crystal, plastic (e.g. polyethylene, polypropylene, polycarbonate), bottles, vials, paper, or envelopes.

The terms "determination of a plurality of cytokines" or "multiple-cytokine-detection" refer to the detection of several cytokines at the same time using a single technique, e.g. the blow technique.

All publications mentioned herein are incorporated in their entirety by reference. Having now generally described the invention, the same will be more readily understood through reference to the following examples, which are provided by way of illustration, and are not intended to be limiting of the present invention, unless specified.

General Procedures

1. Study Group

HIV seropositive patients, including controllers and non-controllers group, and highly exposed persistent seronegative (HEPS) subjects were recruited in a single center (Hospital Universitari Germans Trias i Pujol, Badalona, Spain). HIV controllers were defined as subjects with viral loads below 2,000 copies/mL in the absence of anti-retroviral treatment and CD4+ counts >400 cells/mm$^3$ during at least the last 3 years. The non-controllers were defined as untreated individuals with plasma RNA >50,000 HIV RNA copies/mL and CD4+ counts <300 cells/mm$^3$. A fully developed Western blot analysis was performed to ensure that the non-controller group included subjects with a high viral load identified in an acute phase of HIV infection.

2. PBMCs Extraction

Peripheral blood mononuclear cells (PBMCs) were separated from anticoagulated fresh whole blood by density gradient centrifugation (Leucosep tubes).

3. Cell Culture and Peptide Stimulation

Fresh isolated PBMCs (500,000 cells/well) were culture in 48-well flat plate in a RPMI medium plus 10% fetal bovine serum (FBS), plus antibiotics during 6 h for cytokine intracellular staining or 5 days for cytokine supernatant detection. Cells were stimulated with p24 toggle peptides at final concentration of 2 mg/mL of each sequence and incubated (37° C. 5% $CO_2$). Anti-CD3 plus anti-CD28 magnetic beads were used as a positive control, and RPMI as negative control.

4. Flow Cytometry

Fresh PBMCs (500,000 cells per well) were stimulated by toggle peptide, anti-CD3/CD28 magnetic beads or PBS1x and coestimulated using CD49d and CD8 antibodies (Becton-Dickinson Labware Inc., Franklin Lakes, N.J., US) for 6 hours with GolgiStop (Becton-Dickinson Labware Inc., Franklin Lakes, N.J., US). Also anti-CD107a was added during this period. After 6 hours of incubation the cultures were kept over night into the fridge until cytokine intracellular staining. For routine analyses permeabilized fixed cells (Invitrogen Corp., Carlsbad, Calif., US) were evaluated by flow cytometry for expression of CD3, CD4, CD8 and Th1, Th2 and Th17 cytokines. The following antibodies were used in various combinations to evaluate multiple functions of peptide-stimulated T cells: CD3-PE, CD4-APC, CD8-V500, CD14-V450, CD19-V450, LiveDead, CD107a-PeCy5, IFN-c-FITC, IL-2-FITC, TNFa-FITC, MIP1b-FITC, IL4-PECy7, IL10-PECy7 and IL17-PECy7 (Becton-Dickinson Labware Inc., Franklin Lakes, N.J., US). Cells were collected on an LSR II instrument (Becton-Dickinson Labware Inc., Franklin Lakes, N.J., US) configured to detect 8 color parameters, and analysis was performed using FACSDiva software. After gating, background responses detected in negative control tubes were subtracted from those detected in stimulated samples for every specific functional combination.

5. IFN-γ ELISpot

IFN-γ ELISpot assays were performed as described previously. See Harlow E, Lane D, "Antibodies: A Laboratory Manual" (Cold Spring Harbor Laboratory Press, Cold Spring Harbor, N.Y., US, 1988). Briefly, ELISpot plates (Millipore Corp., Bedford, Mass., US were coated with antihuman IFN-γ mAb overnight at 4° C. The plates were blocked with 100 μL of PBS supplemented with 1% FCS. PBMCs (100,000 cells/100 μL per well) were incubated with stimulation of 0.2 mg/mL of SL9 and GL9 during 16 h. PHA (5 μg/mL) was included as positive control. Capture IFN-γ was detected at sites of secretion by incubation with antihuman IFN-γ conjugated with biotin at room temperature for 1 h. After 6 washes with PBS, streptavidin conjugated with ALP was incubated at room temperature during 45 min. After extensive washing with PBS, TRIS chloride with NBT and substrate were added. The reaction was stopped with Tween 30 min after.

Thresholds for positive responses were determined as exceeding 5 spots (50 SFC/$10^6$) per well and responses exceeding "mean of negative wells plus 3 standard deviations" and "three times mean", whichever was higher.

6. Patients

HIV seropositive subjects (n=17), including Controllers (n=10) and Non-Controllers (7), Highly Exposed Persistent Seronegative (HESN) subjects (MSM, male who have sex with men, n=8; heterosexual with serodiscordant partner n=3) and HIV unexposed individuals (n=4) were recruited at the Hospital Universitari Germans Trias i Pujol, Badalona, and the BCN Checkpoint community center, Barcelona, Spain. HIV Controllers were defined as subjects with viral loads below 2,000 copies/ml in the absence of anti-retroviral treatment and CD4+ counts >400 cells/mm3 during at least the last 3 years. The Non-Controllers were defined as HAART untreated individuals with plasma RNA >50,000 HIV RNA copies/ml and CD4+ counts <300 cells/mm3 and with a fully developed western blot to ensure that they were not high viral load subjects identified in acute phase of HIV infection (Table I). HESN were identified from a high-risk cohort of men having sex with men (MSM) followed a on 3 monthly basis at Checkpoint, a MSM Community center in Barcelona. The study was approved by the local research ethics committee and all participants provided written informed consent.

7. Cell Culture

For all assays, freshly isolated PBMCs were used within 4 h of venipuncture. For Flow cytometric and FlowCytomix studies, 500,000 cells/well were added to 48-well flat plates in a RPMI medium plus 10% FCS, plus antibiotics during 6 h for cytokine intracellular staining (see section Boosted Flow Cytometry) or 5 days for cytokine supernatant detection (see section FlowCytomix). Cells were stimulated with individual p24 toggle peptides at final concentration of 14 ug/ml of each sequence and incubated at 37° C. 5% CO2 until used for corresponding assay. Anti-CD3 plus anti-CD28 magnetic beads (Invitrogene) or PMA (or phorbol 12-myristate 13 acetate) (10 ng/m1) plus Ionomicine (Io) (1 uM) were used as positive controls. As additional positive controls for viral peptide stimulation, EBV MHC class I restricted peptide pool (EBV pool 1) and EBV MHC class II restricted peptide pool (EBV pool 4) for CD8 T cell and CD4 T cell stimulations, respectively, were used at final concentration of 10 ug/ml.

8. FlowCytomix Analyses

In culture supernatants harvested after 5 days, 13 cytokines were detected using a flow-based approach as per manufacturer's description. Human Th1/Th2/Th9/Th17/Th22 13-plex Kit FlowCytomix (eBioscience) is a bead-based analyte detection system for quantitative detection of human IFNγ, IL-1β, IL-2, IL-4, IL-5, IL-6, IL-9, IL-10, IL-12p70, IL-13, IL-17A, IL-22 and TNFα by Flow Cytometry. In brief, fluorescent beads with different sizes and spectral addresses are coated with antibodies that react specifically against the different cytokines to be detected. The mix of coated beads for each cytokine is incubated with samples during 2 hours at room temperature. A biotin conjugated second antibody is added and incubated during 1 h at room temperature before Streptavidin-Phycoerythrin is added to detect and quantify different cytokines based on the bead size and their specific emission spectrum. For antigen specific responses, the median levels (pg/ml) of non-stimulated cultures for each cytokine across all patients was applied as a cut off for positive responses.

9. Boosted Flow Cytometry

Figure 5:
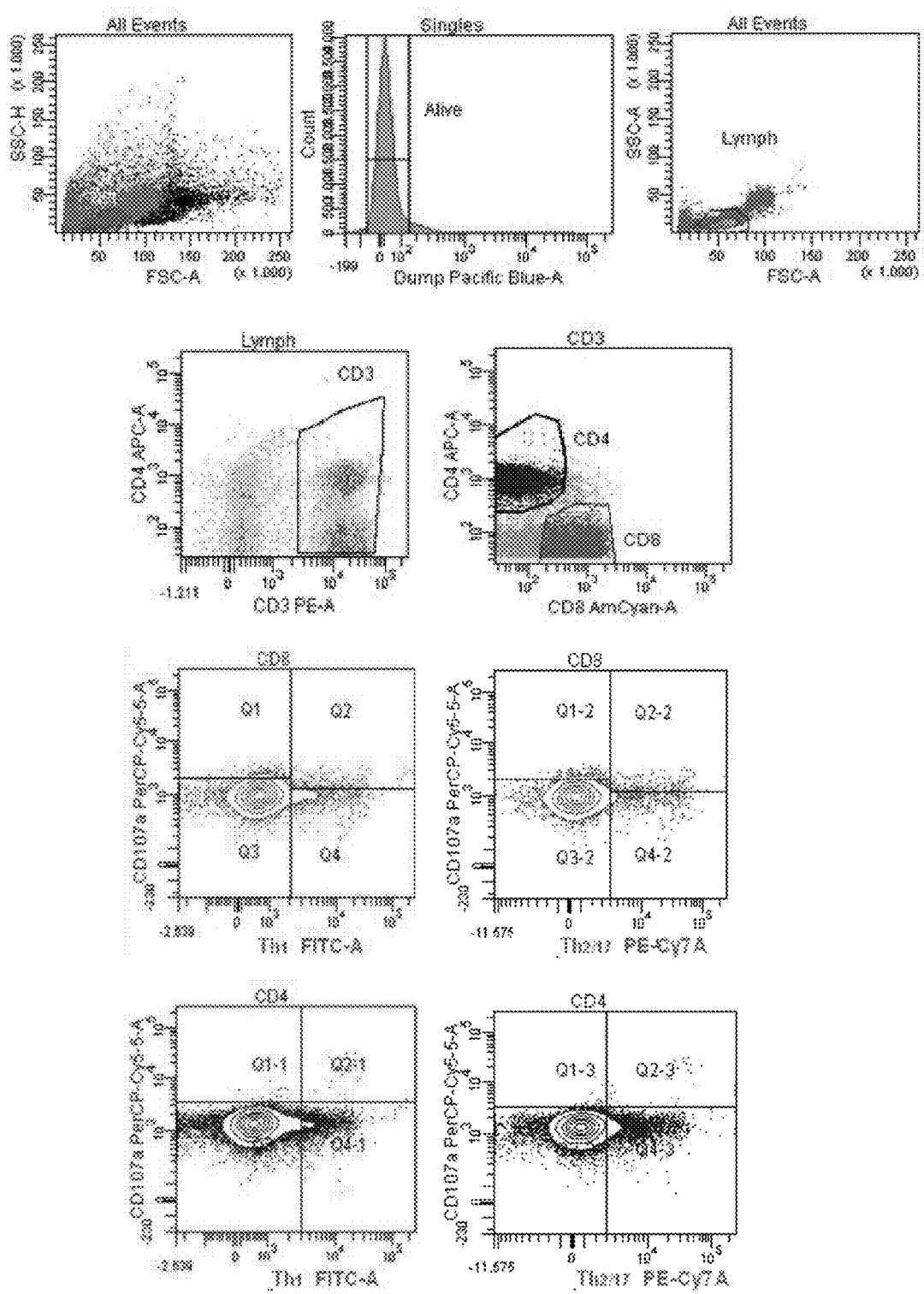
FIG. 5. Gating Strategy for "boosted" flow cytometry (B-flow). Representative example of a gating strategy for CD4 helper T cells and CTL responses upon Toggled peptide stimulation. (See General procedure section)

The boosted flow cytometry approach is based on the intracellular cytokine protocol previously described for polyfunctionality studies (Lamoreaux, L. 2006. Nat Protoc. 1:1507-1516), with a few modifications. Briefly, fresh PBMCs (500,000 cells per well) were stimulated with individual Toggle peptides and CD49d and CD28 antibodies (Becton Dickinson, Mountain View, Calif.) for 6 hours in the presence of GolgiStop and an anti-CD107a antibody (Beckton Dickinson). After 6 hours of incubation the cultures were kept overnight at 4° C. until intracellular cytokine staining. After cell washing, the violet amine reactive dye for viability staining (LIVE/DEAD® Fixable Dead Cell Stain Kit, Invitrogene) was added before cells were stained for T cells markers (CD3 PE, CD4 APC and CD8 V500 from Becton Dickinson) and for exclusion of B lymphocytes and myeloid cells using CD19-V450 and CD14-V450 (Becton Dickinson), respectively. For intracellular cytokines staining, a fixation and permeabilization step (Fix and Perm kit from Invitrogen) was followed by staining with antibodies against Th1 cytokines conjugated with FITC (IFN-γ, IL-2, TNFα and M1P1β) and with antibodies against Th2/17 cytokines conjugated with Pe-Cy7 (IL-4 (eBioscience), IL-10 and IL-17 (Biolegend)). Cells were collected on an LSR II instrument (Becton Dickinson) configured to detect 8 color parameters, and analysis was performed using FACSDiva software. Among the live CD14– and CD19– cells from the singlets, helper T cells (CD3+CD4+) and CTLs (CD3+CD8+) were gated and the cytokine secretion pattern (Th1-like and/or Th2/17 like) plus the degranulation capability (CD107a+) determined (supplementary FIG. 5). After gating, background responses detected in negative control cultures were subtracted from those detected in stimulated samples for every specific functional combination. The inclusion of several cytokines into the same channel boost the signal, but also the background implying the application of very restrictive cutt-offs. As described by Roederer et al (Roederer, M. 2011. Cytometry A. doi: 10.1002/cyto.a.21015), responses that could be detected after thresholding the data from background subtraction were consider positive signals.

10. IFNgamma (or IFN-γ) ELISPOT

Freshly isolated PBMC (100,000 PBMC cells/well) were added in 140 ul of R10 96-well polyvinyl plates (Millipore, Bedford, Mass.). The IFN-γ Mabtech kit was used following manufacturer instructions and as described previously (Frahm, N. 2007. Jour of Immunol). The threshold for positive responses was defined as at least 5 spots per well and responses exceeding the "mean number of spots in negative control wells plus 3 standard deviations of the negative control wells" and "three times the mean of negative control wells", whichever was higher.

11. Statistical Analysis

Statistical analyses were performed using Prism Version 4, GraphPad Prism. After background correction of boosted flow assays, data were thresholded following the analysis procedures previously described (Roederer, M. 2011. Cytometry A. doi: 10.1002/cyto.a.21015). χ-square test was applied for detection of differences among the quality of positive responses detected. For specific comparisons, non-parametric Mann-Whitney test was applied as indicated. In all the analysis, p-value <0.05 was considered statistically significant. Mann-Whitney test was applied. χ-square test was applied. In all the analysis p-value <0.05 was considered statistically significant.

EXAMPLES

Example 1

HIV seropositive patients (n=18, controllers and non-controllers) and highly exposed persistent seronegative subjects (n=8) were analyzed according to the general procedures above.

The IFN-γ ELISpot assay showed higher responses, in terms of magnitude and breath, in HIV patients. No statistically significant differences between the controller and non-controller groups of patients were observed. In addition, fewer responses were detected in the HEPS group. See FIG. 1.

Figure 2:
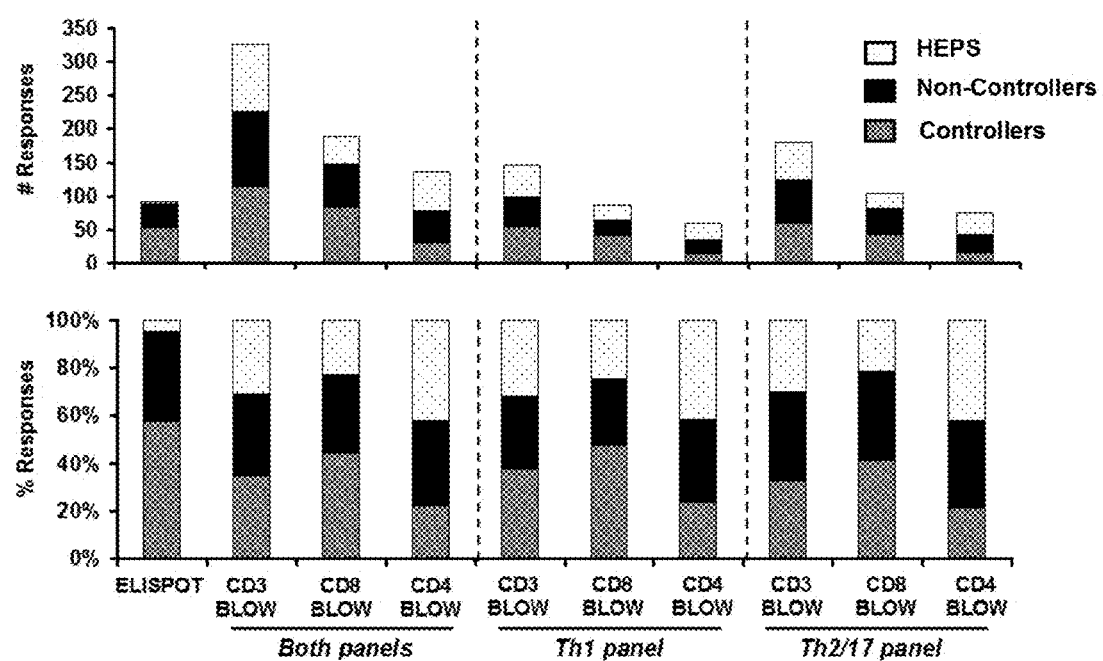
FIG. 2. Histograms (up: absolute numbers and down relative percentages) showing the different responses detected in HEPS and HIV infected patients (Controllers and Non-controllers) when using the IFNγ Elispot and the boosted flow cytometer approaches. Moreover all the boosted flow responses (left), those driven by CD3 lymphocytes, or only CD4 and CD8 T cells are also split among the Th1-like responses (middle) and Th2/17 responses (right). Comparison between "Blow" and ELISpot IFN-γ assays. Significantly more responses were detected with the "Blow" assay compared to the IFN-γ assay. In addition to a general CD8 response, the "Blow" assay recognized specific Th1 and Th2 type responses against Toggle peptides in CD8 and CD4 T cell populations. The increased detection rate was particularly pronounced in the HEPS group.

The generation of additional responses generated to toggled peptides spanning p24, Th1-like (IFN-γ, TNF-α, MIP1-β, IL-2) or Th2-like (IL-4,-10) and Th17 (IL-17) responses on CD8+ and CD4+ T cells were studied by a "Blow". Briefly, this assay is based on the detection of boost cytokines in the same channel of fluorescence by flow cytometry. The Th1-boosted "Blow" analysis detected significantly more Th1-like responses compared to ELISpot assay with higher relevance in the detection of positive responses in the HEPS population. In general, "Blow" analysis detected significantly more responses compared to IFNγ Elispot assay. In addition to the IFNγ CD8 responses measured by IFNγ Elispot, the "Blow" analyses also distinguish "Th1" and "Th2/17" like responses against Toggle peptides in CD8 and CD4 T cell populations. The increased detection rate was particularly pronounced in HEPS. See FIG. 2.

Figure 3A:
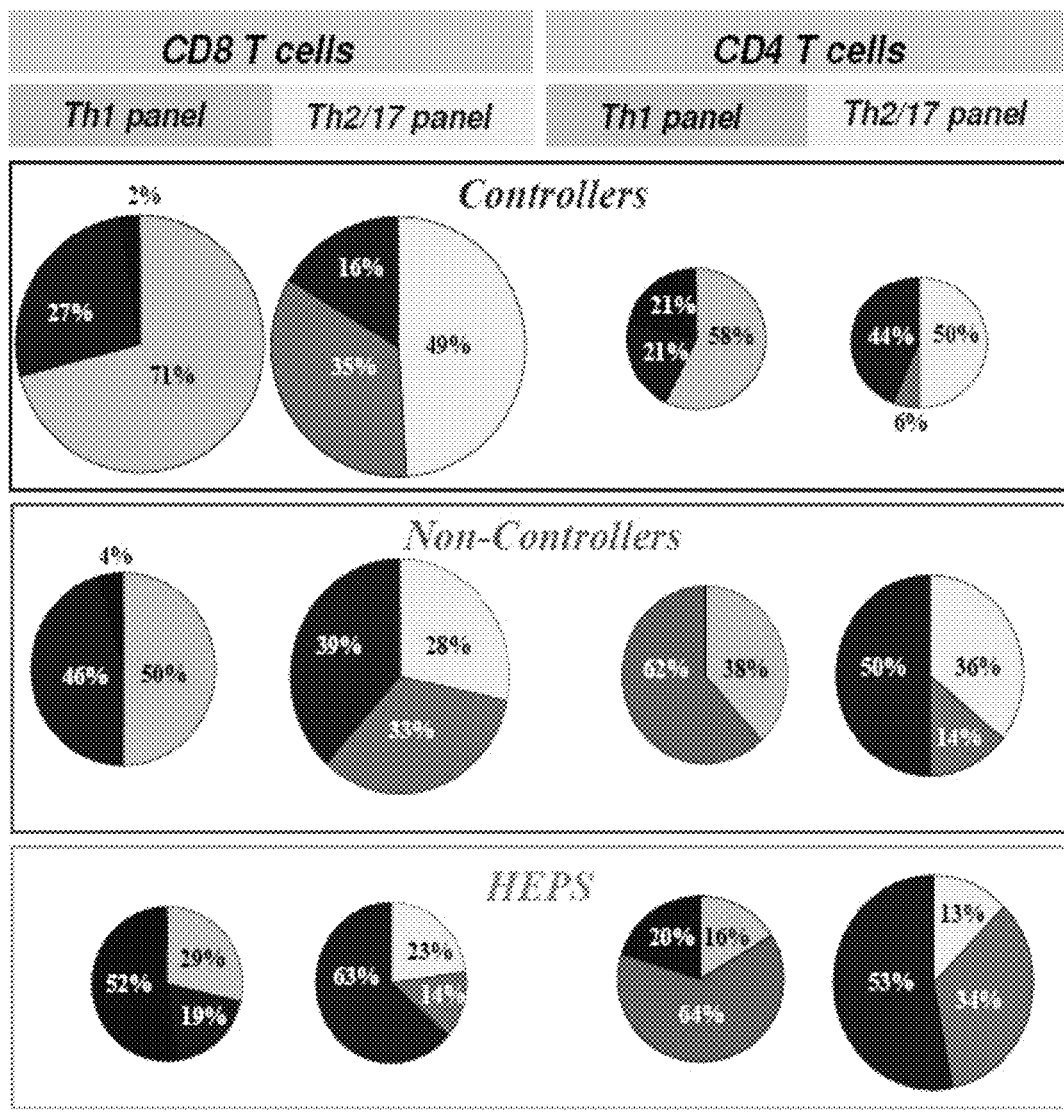
FIG. 3. A-B: CD8 and CD4 "Blow" responses. HIV infected patients generated mostly CD8 responses, while the HEPS population mounted a larger CD4 T cell response. The response profile in HIV controllers, non-controllers and HEPS subjects varied widely in their Th1 versus Th2/IL-17 patterns and their degranulation capacities, both for CD4 and CD8 T cells. In contrast to HIV infected individuals, the CD8 T cell responses in HEPS subjects were often cytokine producing (Th1+ and Th2/17) but did not degranulate (CD107−). The frequent Th2 profiles observed in this population could however be biased by the inclusion of IL-17 in the same panel.
Figure 4A:
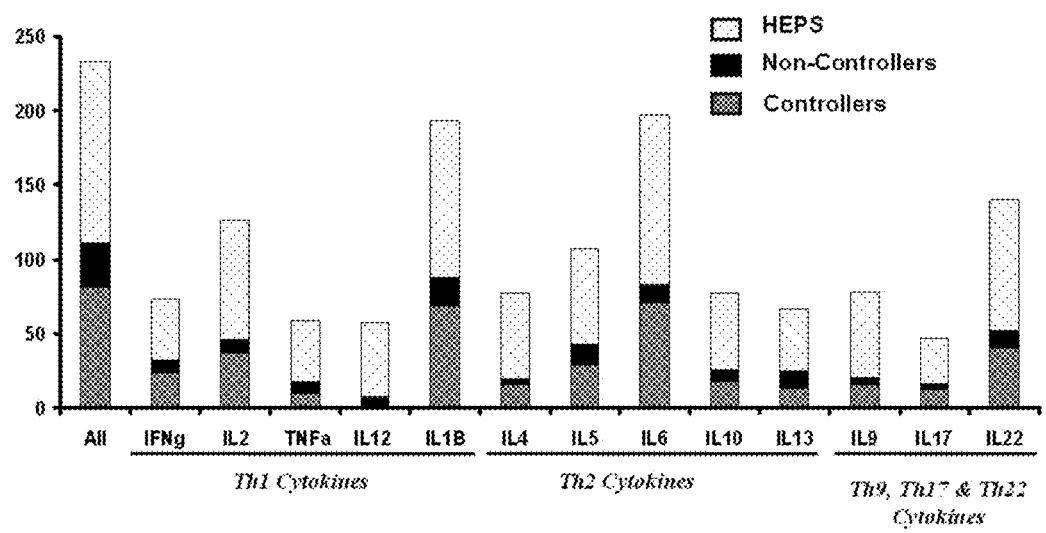
FIG. 4. A-D: Production of individual cytokines was assessed by flow cytometry. The flow-cytomix deconvolution showed a higher number of responses in HEPS subjects compared to HIV+ individuals (i.e. the controller group produced more responses than the non-controller group). Moreover, elevated levels of single cytokines (with statistical significance for IL-1b, IL-10, IL-13 and IL-22) in HEPS subjects compared to HIV+ individuals were also detected.
Figure 4B:
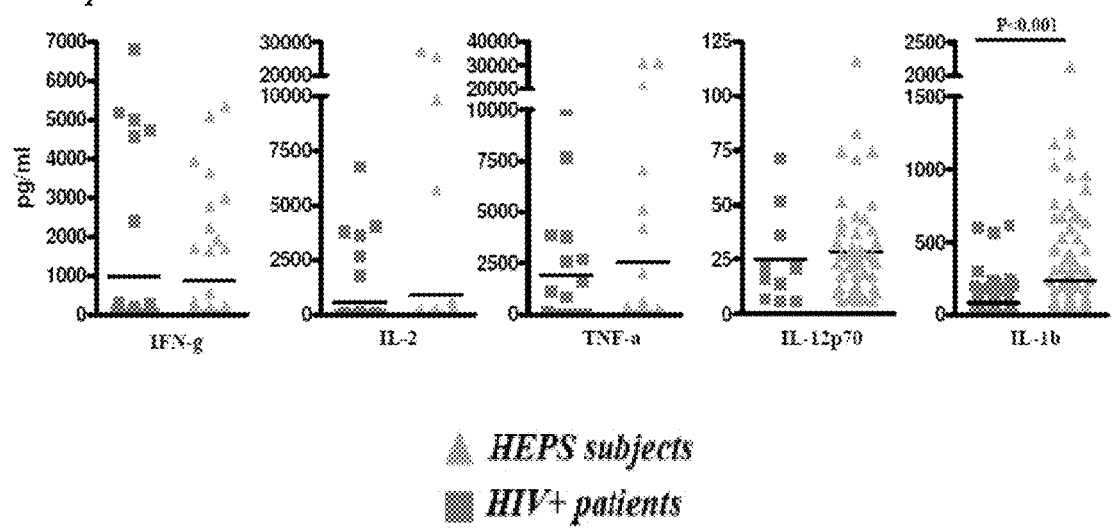
Figure 4C:
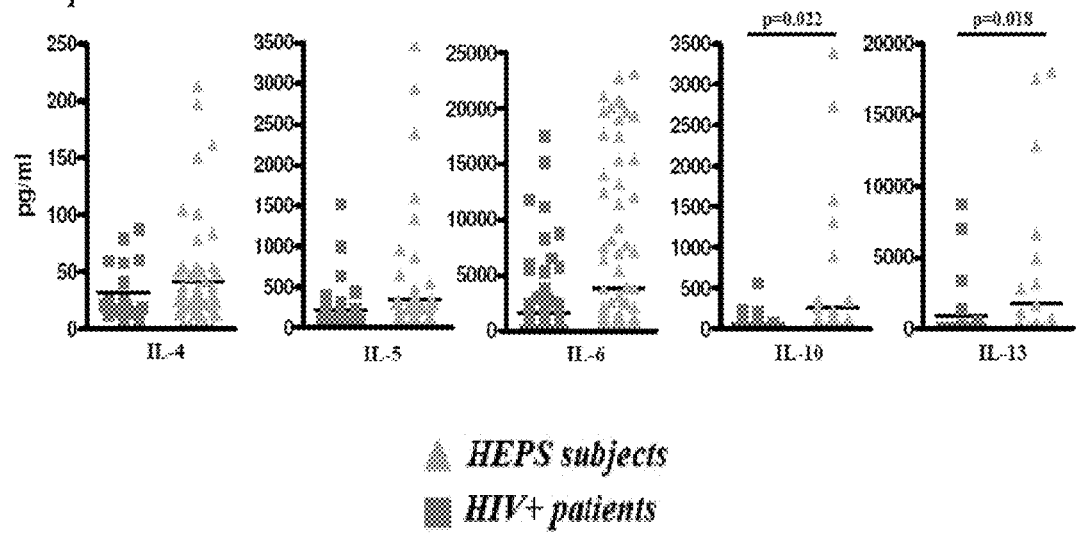
Figure 4D:
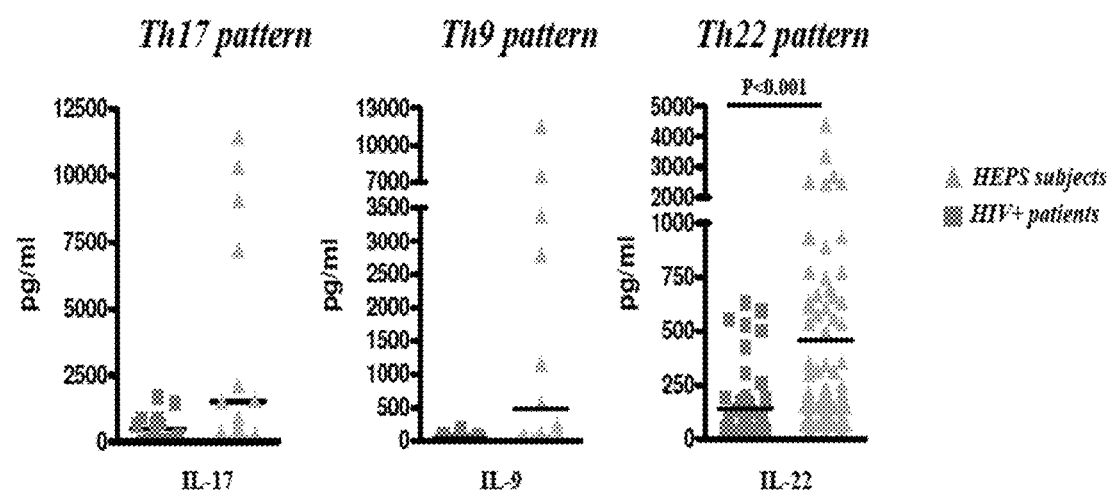

After measuring all the CD4 and CD8 responses generated, it could be observed that while the HIV infected patients generated mainly CD8 responses, the HEPS population produced mostly a CD4 T cell response. See FIG. 3A. Moreover, the response profiles in HIV controllers, non-controllers and HEPS subjects varied widely in their Th1 versus Th2/IL-17 patterns and their degranulation capacities, both for CD4 and CD8 T cells (CD4Th1: $\chi^2$=12.59, p=0.013; CD4Th2: $\chi^2$=11.04, p=0.026; CD8Th1: $\chi^2$=33.16, p=1.107e-06; CD8Th2: $\chi^2$=15.90, p=0.003). See FIG. 3B. Noticeably, the CD8 T cell responses in HEPS individuals were often (52% in Th1 and 63% in Th2/IL17) cytokine producing but did not degranulate (CD107−) in comparison to HIV patients. The frequent Th2 profiles observed in this population could however be biased by the inclusion of IL-17 in the same panel.

As a comparison, the production of individual cytokines was assessed by a 13 cytokines FlowCytomix and ELISpot IFN-γ. Indeed, subsequent flow-cytomix deconvolution showed an elevated level of cytokines (i.e. IL-17, IL-22, IL-9) in HEPS subjects compared to HIV+ individuals. See FIGS. 4 A-D.

Example 2

Figure 6:
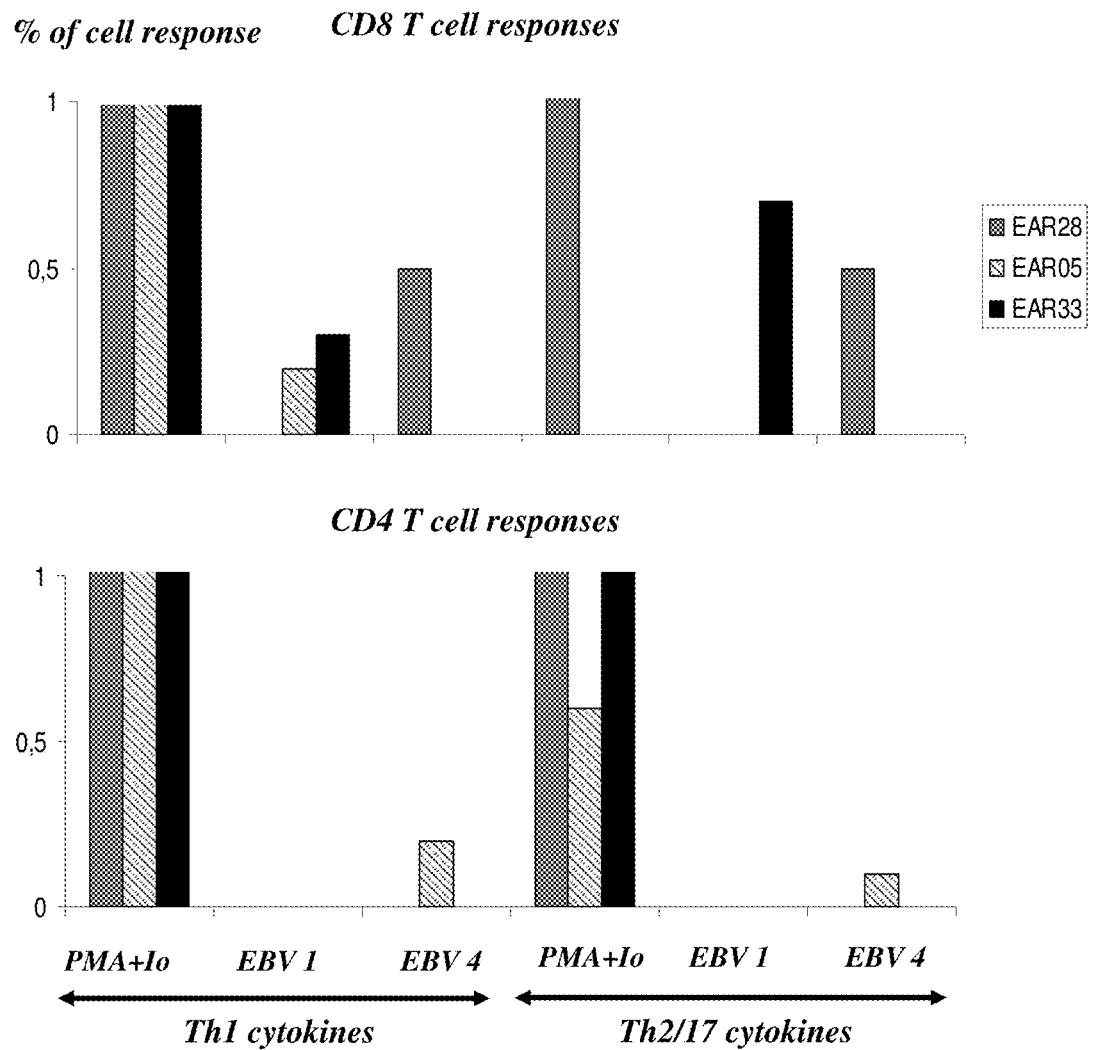
FIG. 6. Percentage of CD8 T cell (up) and CD4 T cell (down) responses generated upon different stimulations in 3 HEPS (serodiscordant couples: EAR28, EAR05 and EAR33). Stimulations: PMA+Io (polyclonal stimulation), EBV pooh (HLA class I restricted peptides). EBV pool4 (HLA class II restricted peptides)
Figure 7:
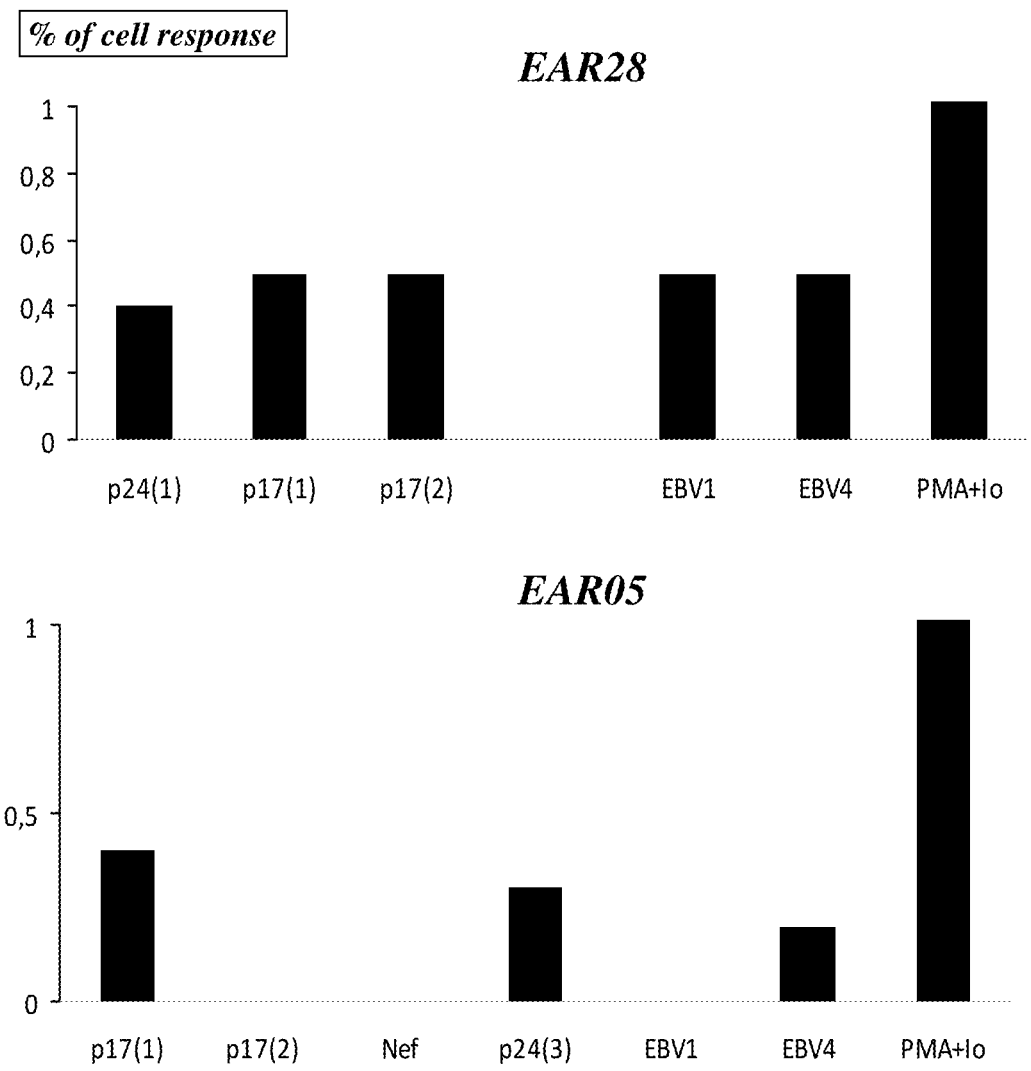
FIG. 7. Percentage of T cell responses generated upon different stimulations in 2 HEPS (serodiscordant couples: EAR05 and EAR28). Stimulations: HIV p24 pool 1, HIV p24 pool 3-, HIV p17 pool 1, -HIV p17 pool 2, Nef pool, EBV pooh (HLA class I restricted peptides), EBV pool4 (HLA class II restricted peptides), PMA+Io (polyclonal stimulation)

A similar experiment as shown in example 1 has been repeated, but using PMA+Io or EBV-derived antigens as positive controls (see FIGS. 6 and 7), or a different HIV-derived antigen like p17. The use of the polyclonal stimulus PMA+Io generates higher positive responses in HEPS than the peptide specific stimulations. However, through the use of pools of EBV peptides, positive responses can also be detected. Moreover, by using the boosted flow cytometry method, we were able to detect responses to pools of HIV peptides in HESN individuals (serodiscordant couples) similar to the responses detected after stimulation with pools of EBV peptides. Finally, the present invention allows for the determination of specific peptidic responses in CD4 (MHC class II peptides) as well as in CD8 (MHC class I peptides) and capture responses against HIV in HESN not observed so far.

The invention claimed is:

1. A method for assaying the T cell response specific against a pathogen in a subject which comprises: i) contacting a sample comprising T cells from the subject with a composition comprising an antigen from the pathogen and ii) determining the levels of a plurality of cytokines produced by the T cells in the sample,
   wherein the levels of the plurality of cytokines are determined by boosted flow cytometry, said boosted flow cytometry comprising detecting several cytokines in the same channel of fluorescence.

2. The method according to claim 1 wherein the composition comprising an antigen is an antigen or a library of antigens.

3. The method according to claim 2 wherein the antigen or the library of antigens from the pathogen is a peptide variant or a library of peptides variants derived from a polypeptide of the pathogen.

4. The method according to claim 3 wherein the library of peptides variants is a toggled peptide.

5. The method according to claim 4 wherein the pathogen is HIV or EBV.

6. The method according to claim 5 wherein the peptide variants derive from the Gag or the Nef polyprotein.

7. The method according to claim 6 wherein the peptide variants derive from p24 or p17.

8. The method according to claim 1 wherein the plurality of cytokines are selected from the group consisting of cytokines characteristic of a Th1 response, cytokines characteristic of a Th2 response and both.

9. The method according to claim 8 wherein the cytokines characteristic of a Th1 response are selected from the group consisting of IFN-γ, TNF-α, MIP1-β, IL-2, IL-12 and IL-1B.

10. The method according to claim 8 wherein the cytokines characteristic of a Th2 response are selected from the group consisting of IL-4, IL-5, IL-6, IL-10, and IL-13.

11. The method according to claim 8 wherein the cytokines characteristic of a Th1 response, the cytokines characteristic of a Th2 response or both are determined in CD4+ cells and/or in CD8+ cells.

12. The method according to claim 8 further comprising determining the levels of cytokines characteristic of a Th9, Th17 or Th22 response.

13. The method according to claim 1 wherein the sample containing T cells is a PBMC preparation.

* * * * *